[54] PHARMACEUTICAL COMPOSITION CONTAINING THE N-METHYL-D-GLUCOSAMINE COMPLEX OF 4-METHYLURACIL AND USE THEREOF

[76] Inventors: Valter Osvaldovich Kulbakh, Bukharestskaya ulitsa, 86, korpus 1, kv. 85; Inesa Vladimirovna Popova, Vasilievsky ostrov, 2 liniya, 25, kv. 27, both of Leningrad, U.S.S.R.

[22] Filed: Aug. 8, 1975

[21] Appl. No.: 603,112

Related U.S. Application Data

[62] Division of Ser. No. 349,670, April 9, 1973, Pat. No. 3,912,714.

[52] U.S. Cl. .................................. 424/180; 536/55
[51] Int. Cl.$^2$ ......................................... A61K 31/70
[58] Field of Search ................................. 424/180

[56] References Cited
UNITED STATES PATENTS 3,468,759   9/1969   Skoda et al. ................. 260/211.5 R

*Primary Examiner*—Lewis Gotts
*Assistant Examiner*—Cary Owens
*Attorney, Agent, or Firm*—Haseltine, Lake & Waters

[57] ABSTRACT

The present invention relates to a novel substance, viz. the N-methyl-d-glucosamine complex of 4-methyluracil of the formula:

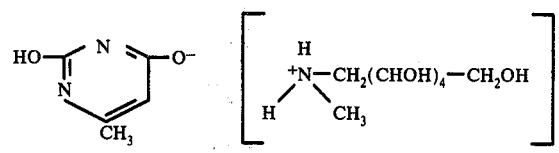

a process for producing same, and use thereof.

The method for producing said substance consists in reacting 4-methyluracil with an equimolar amount of N-methyl-d-glucosamine in an aqueous medium at a temperature of from 20° to 50° C, followed by isolation of the desired product from the solution.

The N-methyl-d-glucosamine complex of 4-methyluracil possesses a pharmacological activity and is useful in medicine as a medicated compound which is a cell-growth biostimulator increasing unspecific immunity and accelerating reparative regeneration of macroorganism tissues. The medicated compound has a high activity, sufficiently wide range of therapeutical applications, and a low toxicity.

Said complex may be also useful as a growth stimulator for baking, nutrient, and other yeast.

7 Claims, No Drawings

PHARMACEUTICAL COMPOSITION CONTAINING THE N-METHYL-D-GLUCOSAMINE COMPLEX OF 4-METHYLURACIL AND USE THEREOF

This application is a divisional application of Ser. No. 349,670, filed Apr. 9, 1973 now U.S. Pat. No. 3,912,714, issued Oct. 14, 1975.

The present invention relates to a novel compound, viz. the N-methyl-d-glucosamine complex of 4-methyluracil, a method for producing same, and use thereof.

Said compound, according to the invention, has the following formula:

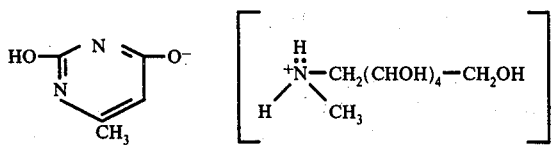

Said novel compound comprises a white or yellowish water-soluble, hygroscopic, crystalline powder with a faint peculiar odor.

The N-methyl-d-glucosamine complex of 4-methyluracil possesses pharmacological activity and is useful in medicine as a medicated compound stimulating unspecific immunity and reparative regeneration of macroorganism tissues. Moreover, said compound may find application as a growth-stimulator for baking, nutrient, and other yeast.

According to the present invention, the N-methyl-d-glucosamine complex of 4-methyluracil is produced by reacting 4-methyluracil with an equimolar amount of N-methyl-d-glucosamine in an aqueous medium at a temperature of from 20° to 50° C. The resulting desired product is isolated from solution by crystallization on cooling or by sublimation drying with preliminary mechanical sterilization and freezing of said solution.

As has been mentioned hereinbefore, the N-methyl-d-glucosamine complex of 4-methyluracil is an active principle of a medicated compound comprising a cell-growth stimulator. This medicated compound is used in such cases where it is necessary to stimulate unspecific immunity and reparative regeneration of tissues at ulceration including ulcer of the stomach and duodenum, sluggishly healing burning lesions, wounds, bone fractures, radiorectitis colpitis cystitis, colitis, and leucopeniae of different etiology.

The medicated compound of the present invention may be administered as a powder of the N-methyl-d-glucosamine complex of 4-methyluracil for oral ingestion or local treatment (by powdering). In the latter case, the medicated compound should be sterile, which is ensured in the process of producing the N-methyl-d-glucosamine complex of 4-methyluracil by mechanical sterilization of an aqueous solution of said substance, followed by freezing of the solution and sublimation drying.

Furthermore, for oral ingestion, the medicated compound may be used in the form of tablets containing 0.25 to 0.5 g of said active principle in combination with a pharmaceutical filler for tablets.

For intramuscular injections and intracavitary introduction, it is recommended to use a medicated compound comprising a 5% solution of the active principle in injection water. Such injection solution may be prepared directly before use by dissolving a sterile powder of the N-methyl-d-glucosamine complex of 4-methyluracil in ampulized water for injections.

Upon testing of the medicated compound of the present invention on animals, it has been found that the N-methyl-d-glucosamine complex of 4-methyluracil stimulates complete restoration of the leucocyte count in peripheral blood of rabbits treated with benzene, hinders the manifastation of nephretoxic action of amphotericine B on rats, stimulates antiviral activity of serum and macrophages of abdominal cavity on mice.

The novel medicated compound is but slightly toxic. The $LD_{50}$ of said medicated compound for intravenous infusion is 2,120 mg per 1 kg of body weight on white mice. White mice show good endurance with respect to the N-methyl-d-glucosamine complex of 4-methyluracil when administered hypodermally, intravenously, intra-abdominally and perorally in doses of up to 1.25 g/kg exceeding the therapeutical dose 500 times. When administered parenterally, the medicated compound exerts no irritating effect on tissues.

When the compound is used as tablets or powder, it is advisable to administer it to adults in doses of 0.25 to 0.5 g 3–4 times per day. A daily dose for children less than one year old is 0.03 g; 1 to 3 years old — 0.05 g; 3 to 8 years — 0.1 g; 8 to 12 years — 0.2 g; 12 years and over — as for adults. Such treatment course takes 10 to 15 days. Since the medicated compound of the present invention has a low toxicity, the treatment course may be prolonged up to 1–1.5 months depending on the disease development.

When the compound is used as a 5% injection solution, the latter should be preferably administered intramuscularly at a rate of 5 ml 2–3 times per day. The same solution in said dosage may be used for injecting round unhealable trophic ulcers and wounds, as well as for washing and rinsing in individually prescribed doses.

Sufficient water-solubility of the N-methyl-d-glucosamine complex of 4-methyluracil (50 to 70 mg/ml which corresponds to a 5 to 7% solution) makes it possible to use it in medicine in small but efficient doses thus giving substantial economy of the medicated compound. The therapeutical range of applications due to said property of the complex is broadened as compared to the prior-art medicated compounds of similar use.

The medicated compound of the present invention has another advantage residing in that unlike the prior-art anabolizators pertaining to the class of steroids, it possesses no side effect.

Contra-indications against the use of the novel medicated compound are malignant diseases of the bone marrow and lymphogranulomatosis.

The medicated compound of the present invention in the powder form may be stored for long periods (for one year) in tightly sealed jars made of orange glass with gaskets of food grade rubber. The medicated compound intended for injections is stored in the form of a sterile powder in flasks in ampules packed in cartons. During storage, the medicated compound does not lose its bio-stimulating activity.

The process for producing the N-methyl-d-glucosamine complex of 4-methyluracil is preferentially realized in the following manner.

N-methyl-d-glucosamine is dissolved in water by stirring, the solution is heated to a temperature of 35 to 40° C and, under vigorous stirring, an equimolar amount of 4-methyluracil is added thereto in increments. The resulting solution is filtered for the separation of solid contaminants and then sterilized through a bacterial filter such as "Millipore". The sterile solution of the N-methyl-d-glucosamine complex of 4-methyluracil thus obtained is then poured into sterilized flasks on a pipetting machine, the solution is frozen in flasks at a temperature of from −30° to −50° C and subjected to sublimation drying. The flasks with the dried powder of the N-methyl-d-glucosamine complex of 4-methyluracil are corked with sterile plugs made of food grade rubber and closed with aluminum cups with subsequent rolling thereof for the purpose of hermetic sealing. After checking the sterility of the prepared lot of the desired product, the flasks with the product are packed in cartons.

The medicated compounds in the form of a sterile powder in flasks and as a solution are intended for intramuscular injections and intracavitary introduction. Moreover, the sterile powder may be used locally for treating wounds, burning lesions, and trophic ulcers by powdering.

In addition to the above-described method of sublimation drying, the resulting N-methyl-d-glucosamine complex of 4-methyluracil may be isolated from an aqueous solution by concentrating the solution with subsequent crystallization upon cooling. The precipitate of said complex is separated from the mother liquor by filtration and dried under vacuum. The resulting powder may be used per se for oral ingestion or may be tableted with a pharmaceutical filler for the same mode of introduction.

For a better understanding of the present invention the following examples illustrating the production of the N-methyl-d-glucosamine complex of 4-methyluracil are given hereinbelow.

EXAMPLE 1

1.95 g (0.01 g-mol) of N-methyl-d-glucosamine were dissolved in 20 ml of water and 1.26 g (0.01 g-mol) of 4-methyluracil was added in increments to the resulting solution while heating the reaction mass to 50° C on a water bath. A clear solution of the resulting N-methyl-d-glucosamine complex of 4-methyluracil was concentrated in two steps and cooled to 10° C. The resulting precipitate of said complex was separated from the mother liquor by filtration and dried under vacuum to give 2.6 g of the N-methyl-d-glucosamine complex of 4-methyluracil powder which corresponded to 81.5% of the theoretical.

EXAMPLE 2

19.5 g (0.1 g-mol) of N-methyl-d-glucosamine were dissolved in 250 ml of water and 12.6 g (0.1 g-mol) of 4-methyluracil was added in increments to the resulting solution. The reaction mass was stirred at 35° C till complete dissolution of the 4-methyluracil. In the case of solution turbidity, said solution was filtered to remove mechanical contaminants. Thereafter, the solution of the N-methyl-d-glucosamine complex of 4-methyluracil was subjected to mechanical sterilization through a bacterial filter such a "Millipore". A sterile solution of said complex was poured into sterilized flasks; the solution was frozen in the flasks at a temperature of −40° C and subjected to sublimation drying. 31.5 g of sterile powder of the N-methyl-d-glucosamine complex of 4-methyluracil were thus obtained which corresponded to a yield of 98% of the theoretical.

What is claimed is:

1. A pharmaceutical composition capable of stimulating unspecific immunity of ulcerated tissue comprising an immunity stimulating amount of N-methyl-d-glucosamine complex of 4-methyluracil of the formula:

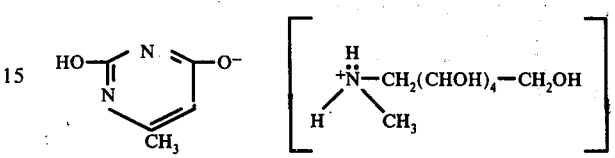

as the active principle.

2. The composition of claim 1, in tablet form containing the active principle in an amount of from 0.25 g to 0.5g in combination with a pharmaceutical filler for tablets.

3. The composition of claim 1 comprising a 5% solution of the active principle in injection water.

4. A method for stimulating unspecific immunity and reparative regeneration of ulcerated tissue consisting essentially of administering to said tissue either orally or by intramuscular injection or by intracavitary introduction a parhmaceutical composition comprising an immunity stimulating or tissue regenerating effective amount of the N-methyl-d-glucosamine complex of 4-methyluracil of the formula:

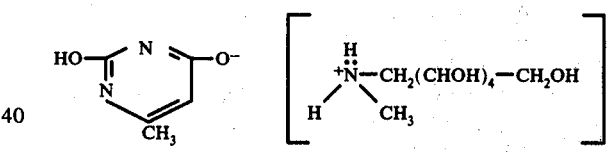

5. A pharmaceutical compositon capable of stimulating reparative regeneration of ulcerated tissue comprising a tissue regenerating amount of N-methyl-d-glucosamine complex of 4-methyl uracil of the formula:

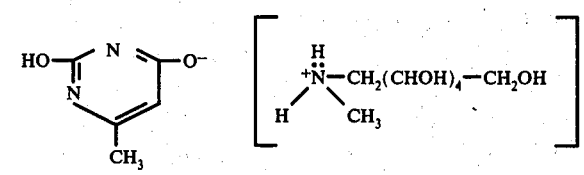

as the active principle.

6. The method of claim 4 wherein the composition is administered orally 3–4 times a day in the form of a tablet containing 0.25 to 0.5 g of said complex.

7. The method of claim 4 wherein the composition is administered intramuscularly at the rate of 5 ml. of a 5% injection solution of said complex 2–3 times a day.

* * * * *